(12) United States Patent
Greneker, III et al.

(10) Patent No.: US 7,199,749 B2
(45) Date of Patent: Apr. 3, 2007

(54) RADAR DETECTION DEVICE EMPLOYING A SCANNING ANTENNA SYSTEM

(75) Inventors: Eugene F. Greneker, III, Marietta, GA (US); Oscar David Asbell, Atlanta, GA (US); Jonathan L. Geisheimer, Mableton, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 130 days.

(21) Appl. No.: 10/735,478

(22) Filed: Dec. 12, 2003

(65) Prior Publication Data

US 2005/0128124 A1 Jun. 16, 2005

(51) Int. Cl.
*G01S 13/62* (2006.01)

(52) U.S. Cl. .......................... 342/22; 342/28; 342/114; 600/534; 340/554

(58) Field of Classification Search ................ 342/22, 342/28, 114, 115, 160, 162; 600/534; 340/554
See application file for complete search history.

(56) References Cited

U.S. PATENT DOCUMENTS

| | | | | |
|---|---|---|---|---|
| 3,875,929 | A * | 4/1975 | Grant | 600/429 |
| 4,958,638 | A | 9/1990 | Sharpe et al. | 128/653 |
| 5,361,070 | A * | 11/1994 | McEwan | 342/21 |
| 5,682,164 | A * | 10/1997 | McEwan | 342/27 |
| 5,766,208 | A * | 6/1998 | McEwan | 600/595 |
| 5,867,257 | A * | 2/1999 | Rice et al. | 356/28.5 |
| 6,031,482 | A | 2/2000 | Lemaitre et al. | 342/22 |
| 6,122,537 | A | 9/2000 | Schmidt | 600/407 |
| 6,208,286 | B1 | 3/2001 | Rostislavovich et al. | 342/135 |
| 6,470,066 | B2 * | 10/2002 | Takagi et al. | 378/8 |
| 6,552,677 | B2 * | 4/2003 | Barnes et al. | 342/22 |
| 6,909,397 | B1 * | 6/2005 | Greneker, III et al. | 342/173 |
| 7,052,469 | B2 * | 5/2006 | Minamiura et al. | 600/534 |
| 7,123,758 | B2 * | 10/2006 | Jeung et al. | 382/128 |
| 2002/0008655 | A1 * | 1/2002 | Haj-Yousef | 342/22 |
| 2002/0105455 | A1 * | 8/2002 | Wright | 342/22 |
| 2002/0196177 | A1 * | 12/2002 | Johansson et al. | 342/22 |
| 2003/0117310 | A1 * | 6/2003 | Kikuchi et al. | 342/22 |
| 2003/0122824 | A1 * | 7/2003 | Chen et al. | 345/428 |
| 2003/0179126 | A1 * | 9/2003 | Jablonski et al. | 342/22 |
| 2003/0189511 | A1 * | 10/2003 | Lasky et al. | 342/22 |
| 2005/0078028 | A1 * | 4/2005 | Cist | 342/22 |

(Continued)

OTHER PUBLICATIONS

"Microprocessor-controlled automatic clutter-cancellation circuits for microwave systems to sense physiological movements remotely through the rubble", Chuang, H.; Chen, Y.; Chen, K. IMTC-90. 7th IEEE Feb. 13-15, 1990 Ps:177-181.*

(Continued)

*Primary Examiner*—John B. Sotomayor
(74) *Attorney, Agent, or Firm*—Thomas, Kayden, Horstemeyer & Risley, LLP

(57) ABSTRACT

Systems and methods for detecting a respiration signal in a target area are disclosed. Briefly described, in architecture, one embodiment of the system, among others, can be implemented as follows. The system includes a scanning antenna configured to transmit a microwave signal across a horizontal axis in the target area. Also, the system includes a control system that tracks the position of the scanning antenna along the horizontal axis. A signal processing system then detects a respiration signal of a living subject in the target area from reflected microwave signals from the target area and the positional data. Other systems and methods are also provided.

33 Claims, 16 Drawing Sheets

U.S. PATENT DOCUMENTS

2005/0128123 A1* 6/2005 Greneker et al. ............ 342/22
2005/0128124 A1* 6/2005 Greneker et al. ............ 342/22

OTHER PUBLICATIONS

"Microwave system for the detection of trapped human beings", Aggelopoulos, E.; Karabetsos, E.; Uzunoglu, N.; Constantinou, P. Industrial Electronics, 1995. ISIE '95. Proceedings of the IEEE International Symposium on vol. 1, Jul. 10-14, 1995 Ps:187-192.*

"Microwave life-detection systems for searching human subjects under earthquake rubble or behind barrier", Kun-Mu Chen; Yong Huang; Jianping Zhang; Norman, A. Biomedical Engineering, IEEE TraNs on vol. 47, Issue 1, Jan. 2000 Ps:105-114.*

"A microwave radio for Doppler radar sensing of vital signs", Droitcour, A.; Lubecke, V.; Jenshan Lin; Boric-Lubecke, O. Microwave Symposium Digest, 2001 IEEE MTT-S International vol. 1, 2001 pp. 175-178.*

"0.25 μm CMOS and BiCMOS single-chip direct-conversion Doppler radars for remote sensing of vital signs", Droitcour, A.D.; et al Solid-State Circuits Conf, 2002. Digest of Technical Papers. ISSCC. 2002 IEEE Int'l vol. 1, 2002 Ps:348-349.*

"10 GHz Doppler radar sensing of respiration and heart movement", Lubecke, O.B.; Ong, P.-W.; Lubecke, V.M. Bioengineering Conference, 2002. Proceedings of the IEEE 28th Annual Northeast 2002 pp. 55-56.*

"Range correlation effect on ISM band I/Q CMOS radar for non-contact vital signs sensing", Droitcour, A.D.; Boric-Lubecke, O.; Lubecke, V.M.; Lin, J.; Kovacs, G.T.A. Microwave Symposium Digest, 2003 IEEE MTT-S Int'l vol. 3, Jun. 8-13, 2003 Ps:1945-1948.*

"Wireless vital signal detection systems and its applications at 1.9GHz and 10GHz", Park, J.M.; Choi, D.H.; Park, S.O. Antennas and Propagation Society International Symposium, 2003. IEEE vol. 4, Jun. 22-27, 2003 pp. 747-750.*

"Non-invasive respiratory movement detection and monitoring of hidden humans using ultra wideband pulse radar", Ossberger, G.; et al, R. Joint UWBST & IWUWBS. 2004 Int'l Workshop on May 18-21, 2004 Ps: 395-399.*

"Survivor search radar system for persons trapped under earthquake rubble", Arai, I. Microwave Conference, 2001. APMC 2001. 2001 Asia-Pacific 2001 pp. 663-668 vol. 2.*

"X-ray specs could change the rules of rescue", Anonymous. Design Engineering. Toronto:Aug./Sep. 2003. vol. 49, Iss. 7, p. 22.*

"RADAR flashligh aids police in search for suspects", Anonymous. Microwaves & RF. Cleveland:Jul. 2001. vol. 40, Iss. 7, p. 28 (1 pp.).*

"Hand-held radar device detects breathing, heartbeats", Anonymous. Design News. Boston:Jan. 19, 1998. vol. 53, Iss. 2, p. 36 (1 pp.).*

* cited by examiner

RADAR DETECTION DEVICE EMPLOYING A SCANNING ANTENNA SYSTEM

TECHNICAL FIELD

The present invention is generally related to microwave radar systems and, more particularly, is related to systems and methods for detecting a respiration signal, through a non-conducting intervening wall with a microwave radar system.

BACKGROUND OF THE INVENTION

One recent use of homodyne radar system involves the detection of minute body movements that are associated with human respiratory activity. This approach is based on the principle that breathing produces measurable phase changes in electromagnetic waves as they reflect off of the skin surface of the moving thorax of a living person. When the target surface is moving, as does the surface of the chest in conjunction with respiratory and cardiac activities, corresponding variations will be observed in the difference of the phase between the received and transmitted signal. The observed variations can be used to determine motion-related target parameters such as displacement and velocity.

Given the extreme sensitivity to slight motion that can be sensed with homodyne radar, a device has been developed called a "Radar Flashlight." The Radar Flashlight is designed to allow police or the military to detect the respiration signature of a non-cooperative human subject behind a wall, door or an enclosed space with non-conductive walls. The device also has application to the location of conscious or unconscious persons in a smoke filled or chemical contaminated office building.

Currently, in operation, the Radar Flashlight is placed against the intervening wall or on a tripod and the homodyne radar system is activated by the operator. When the Radar Flashlight is not stabilized by the user pressing it against the wall or by placing it on a stabilizing tripod, the user's slight hand motion is detected by the Radar Flashlight as movement. Thus, when hand motion is present, the homodyne radar cannot effectively determine if the detected movement signature is from the subject or from the stationary wall.

Thus, a heretofore unaddressed need exists in the industry to address the aforementioned deficiencies and inadequacies.

SUMMARY OF THE INVENTION

The present invention provides systems and methods for detecting a respiration signal in a target area while rejecting hand motion clutter. Briefly described, in architecture, one embodiment of the system, among others, can be implemented as follows. The system includes a scanning antenna configured to scan a transmitted continuous wave (CW) microwave signal azimuthally across a horizontal line in the target area. Also, the system includes a control system that tracks the position of the scanning antenna along the horizontal line. A signal processing system then suppresses the hand motion while preserving the respiration signal from a living subject in the target area. The amplitude of the reflected microwave signals from the target area and the positional data of the living subject are displayed to the operator after the cancellation of the self-generated motion clutter.

Another embodiment, among others, of the present invention is a method for detecting a respiration signal in a target area. This method comprises the following steps. A microwave signal is transmitted or scanned azimuthally across the target area along a horizontal scanning line forming an horizontal axis and the position along the horizontal scanning axis (at which the microwave signal is transmitted) is tracked. Further, a reflected microwave signal is received from the target area and the self-generated motion clutter is cancelled leaving the detected respiration signal of at least one subject in the target area.

Other systems, methods, features, and advantages of the present invention will be or become apparent to one with skill in the art upon examination of the following drawings and detailed description. It is intended that all such additional systems, methods, features, and advantages be included within this description, be within the scope of the present invention.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
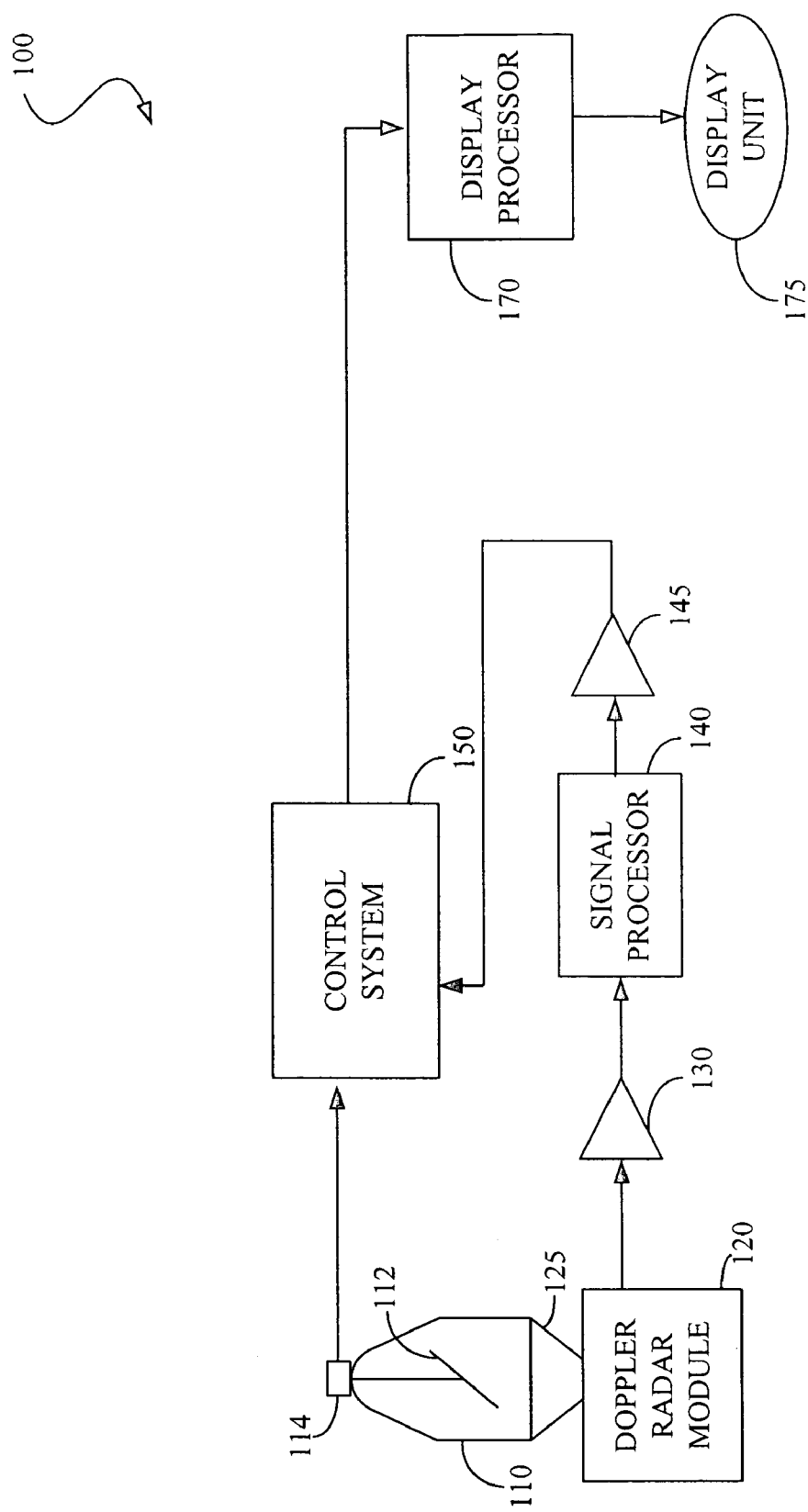
FIG. 1 is a block diagram of one embodiment of a radar detection device of the present invention.

FIG. 1 shows a diagram of a possible embodiment of a radar detection device 100 employing one embodiment of the radar scanning system ("scanner") 10. In this example, the radar detection device 100 comprises a homodyne Doppler radar module 120 that generates a microwave continuous wave (CW) signal at 10.525 GHz. However, other devices 100, systems 110, and microwave frequencies may also be used.

The CW signal is generated using a solid state Gunn device transmitter (not shown). The resulting CW signal is transmitted through a vertical pointing antenna 125. A mechanical scanner 110 is positioned on top of the vertical antenna 125 to make a scanning antenna assembly. Accordingly, a rotating 45-degree mirror 112 inside the mechanical scanner 110 redirects a transmitting microwave beam from the vertical pointing antenna 125 along an azimuthal horizontal axis 90 degrees from the vertical.

The CW microwave homodyne radar operating at 10.525 GHz supplies approximately 30 mW to the antenna 125 and a local oscillator signal of lesser power to an associated mixer assembly (not shown) within the homodyne Doppler radar module 120. The scanner 110 has a digital shaft encoder 114 to track the rotating mirror 112 position. The digital shaft encoder 114 provides position information to the computer control system 150. The computer control system 150 is configured to collect positional data and radar output data as the 45-degree mirror 112 rotates at approximately 1,800 revolutions per minute (PPM) or 30 rounds per second (RPS). The computer control system 150 samples the radar output preferably 512 times for each 360 degrees of mirror 112 revolution using an analog to digital converter capable of digitizing the radar output signal to 16 bits to get the required dynamic range The scanner 110 may be covered across the rear portion of the assembly by radar absorbing material (not shown) to prevent radiation from being emitted except when the 45-degree mirror is pointing around a 180-degree arc toward a target area. This 180 degrees of antenna rotation (where no radiation occurs) can be used to provide the system with a standard reference signal for non-target calibration purposes. Also, the absorption of radar energy over the 180 degrees in the direction of the operator keeps the operator body motion from being detected and reduces exposure of the operator to the radar's energy. In addition, some signal processing can be performed during the dead time when the mirror 112 is pointing into the absorber, during the mirror's rotation over the 180 degrees of absorber covered antenna area. The absorber can be removed to provide a full 360 degrees of coverage when calibration, human microwave exposure, motion, and processing time are not of concern regarding system operation.

When the scanning beam emerges from the absorber-covered area, the beam radiates the microwave energy toward the intervening object, such as a wall or door. The scanning action across the wall or door generates antenna scan modulation due to the changing range between the radar and the wall as the beam scans across the wall. The changes in the return signal amplitude caused by the scan modulation generates features in the graphical pattern of the scan and these features can be used as azimuthal reference points during signal processing to eliminate hand motion artifacts. When a living subject, for example, is located in front of the rotating mirror as the radar detection device 100 scans across the subject, the transmitted signal is reflected off the body of the living subject. Thus, any motion of the subject's body causes a phase shift in the reflected signal proportional to the amount of motion in the radial direction to and away from the radar scanner 110. At a frequency of 10.525 GHz, for example, the typical phase shift is 360 degrees for every half wavelength (1.5 centimeters) of radial motion toward or way from the radar scanner 110.

The radar antenna 125 of the detection device 100 transmits microwave energy in a 16-degree beam forward toward the target area. If a living subject is positioned behind a wall in the target area, a high percentage of the transmitted power incident on the wall is reflected back to the radar detection device 100. In addition, a low percentage of the transmitted power actually penetrates the wall to "illuminate" the subject of interest.

The signal, reflected from the subject, reflects off of the 45-degree mirror 112 and downward to antenna 125. From the antenna 125, the signal is sent to the Doppler radar module 120, where a reference signal from the CW transmitter is mixed with the received signal. A sum and difference signal is generated during the mixing process in typical homodyne fashion. The sum signal is filtered and eliminated while the difference signal is sent to amplifier(s) 130, where the signal is amplified. The gain(s) of amplifier(s) 130 is set so that they do not saturate on the maximum expected signal. The outputs from amplifier(s) 130 may then be fed to a signal processor 140. Typically, a total of 512 points of data are collected during each 360-degree scan of the mirror 112 (above the antenna 125). Given this relationship, one sample point is collected at each 0.7-degree increment of rotation. In a typical data collection sequence, the 512 sample points of signal are stored in a first storage buffer (not shown) that is part of the signal processor 140 during the first revolution of the 45-degree mirror 112. After the next revolution of the 45-degree mirror 112 another 512 sample points are stored in a second storage buffer (not shown). After the next revolution of the 45-degree mirror 112, 512 sample points of signal are stored in a third storage buffer (not shown). In the example case, each 512 point buffer represents 1/30 of a second time history of received data. This process continues until a selected number of antenna rotations have been made, and the data from each has been stored in a 512-point wide storage buffer.

Signal processing is performed on the data stored in the 512-data-point wide buffers by signal processor 140. The data in the consecutive signal storage buffers is capable of being read out one complete 512 point scan at a time to provide a "snapshot" of approximately 1/10th of a second. The scans in the buffer can also be read out in sequential order and plotted on top of each other as will be illustrated. A single sample at a specific sample index number within each of the 512-point buffers can be read out and operated on in a manner to be shown. An indexed single data point within any or all of the 512-point arrays can be read out. Mathematical operations can be performed on the data stored in each array, with the result of the mathematical operation being stored in a holding buffer that is part of the signal processor 140 for display to the operator.

Signal processing algorithms resident in the signal processor 140 extract motion induced phase changes from the received signal. Accordingly, certain signal processing algorithms suppress the self motion of the radar detection device 100 induced by motion of the operator's hand. Other signal processing algorithms may extract the respiration signal or "respiration signature" from the radar output by detecting a very small phase shift between the transmitted and received signal of the radar detection device 100 caused by the motion of the thorax during the respiration cycle of a living subject. The output of the signal processor 140 may be amplified by amplifier 145 and provided to the computer control system 150. With radar output data and the positional data of the radar scanner being collected as the scanner rotates at 600 revolutions per minute (RPM), the computer control system provides this information to a display processor 170 which compiles this information into a graphical output that may be visually presented on the display unit 175.

Figure 2:
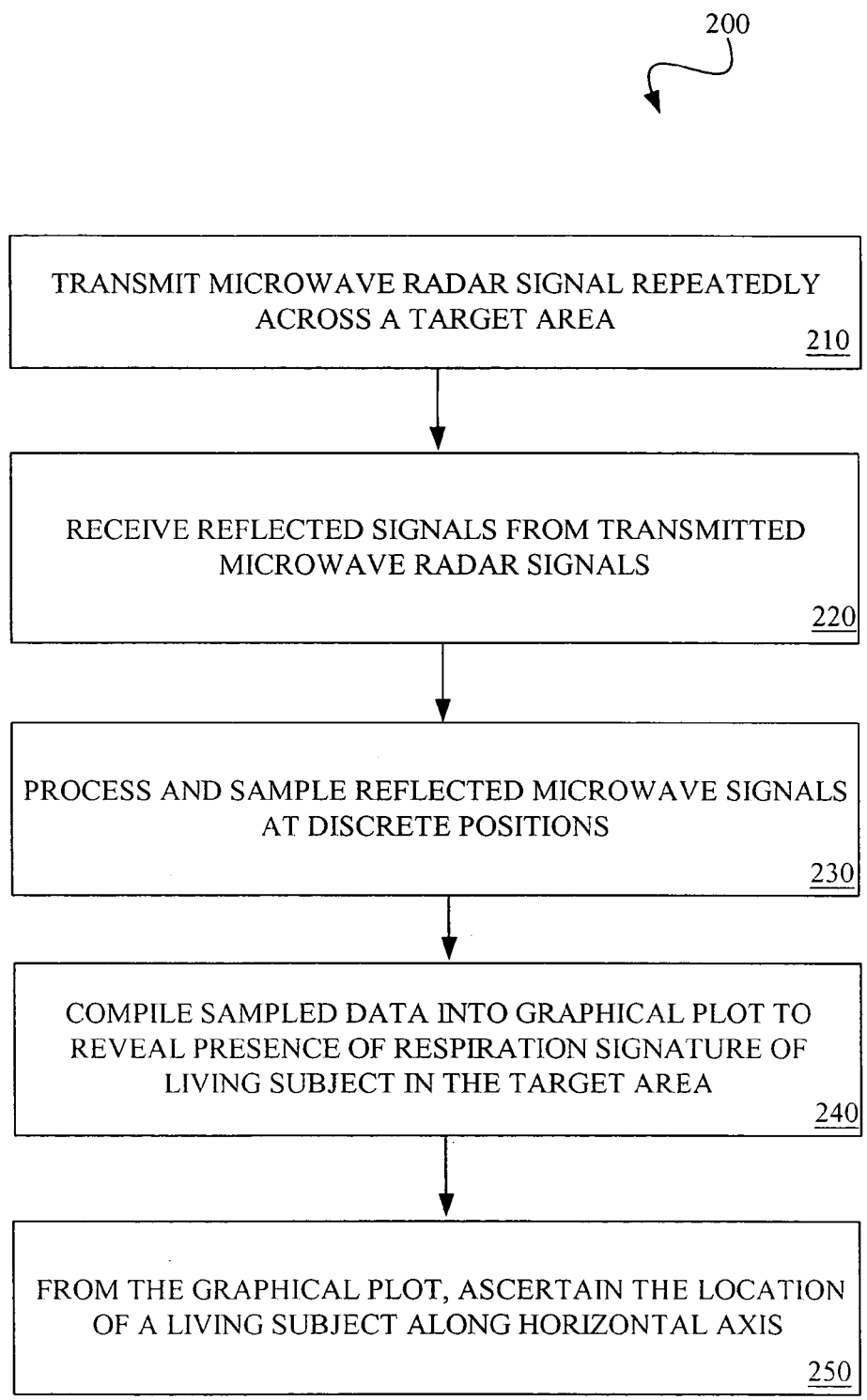
FIG. 2 is a flowchart depicting the functionality of a representative embodiment of the radar detection device of FIG. 1.

As depicted in FIG. 2, the functionality of a representative embodiment of the radar detection device 100 (employing a radar scanner 110) or method 200 may be construed as beginning at block 210. In block 210, a respective signal is continuously transmitted from a Doppler radar module 120 and scanned along a horizontal axis across a target area using a radar scanner 110. In block 220, reflective signals from obstructive object(s) in the target area are received by the Doppler radar module 120. The reflective signals are processed by the Doppler radar module 120 and sampled at discrete antenna positions by the signal processor 140 under control of the computer control system 150, as shown in block 230. Then, in block 240, a large number of the sampled data is processed to remove operator hand motion and compiled into a graphical plot that may reveal the respiration signature of a living subject in the target area, if present. Also, as shown in block 250, the position or location of the subject along the horizontal axis may be ascertained from the graphical plot.

Figure 3:
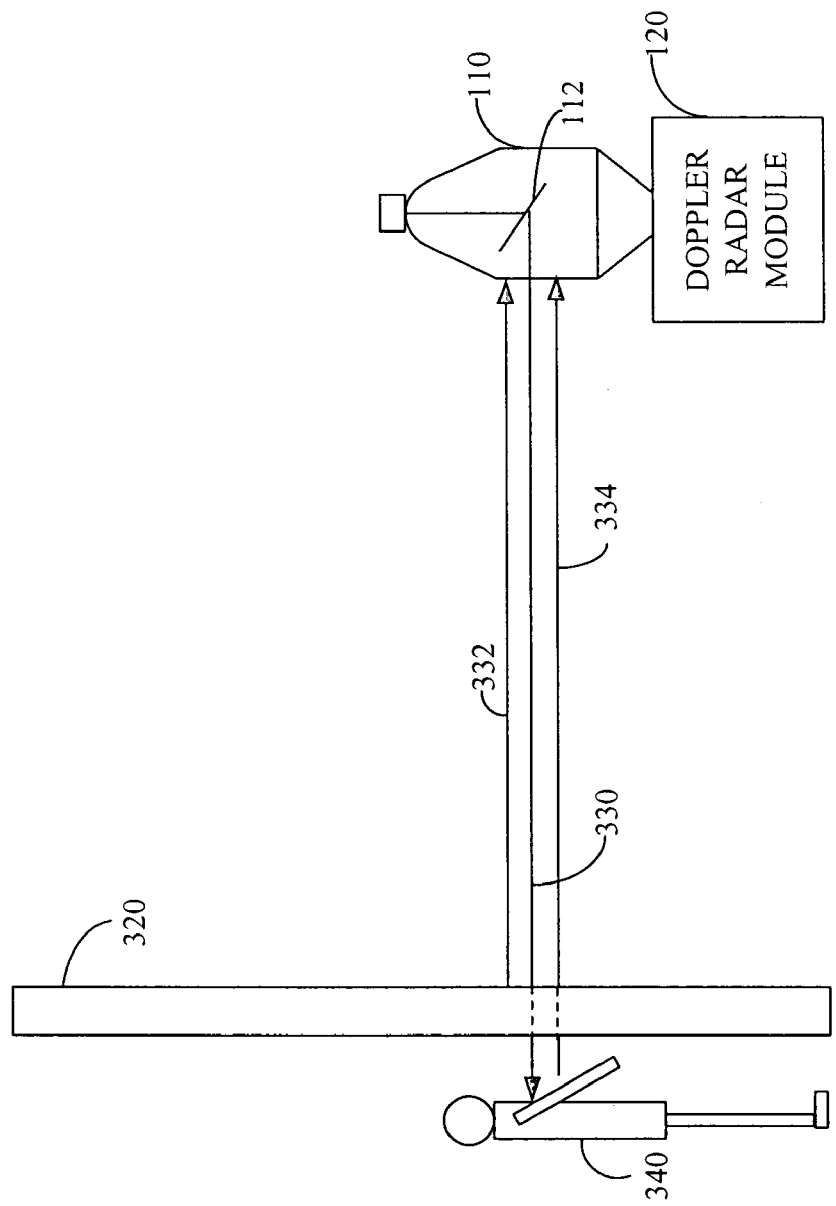
FIG. 3 is a block diagram describing a physical configuration under which the radar detection device of FIG. 1 may be used.

For example, consider FIG. 3. Here a mechanical radar scanner 110 is positioned on top of a Doppler radar module 120. The Doppler radar module 120 transmits a microwave signal 330 off of the mirror 112 toward an opaque reflective surface 320 (e.g, a wall or door) in a target area. For this example, the 45-degree mirror 112 is scanned at a rate of 10 Hz. Note, a living subject, such as a person 340, is positioned behind the opaque reflective surface 320, which in this example is a test wall. This test wall is composed of three sections. A first leftmost section is composed of wood siding on the outside and wallboard on the inside surface. The center second section is a solid wooden door, and the third rightmost section is a brick wall with 2 by 4 headers and wallboard backing.

Therefore, a portion of the transmitted signal 330 is reflected back off of the reflective surface or wall 320 towards the Doppler radar module 120. This reflected signal 332 is detected and received by the Doppler radar module 120. Further, a portion of the transmitted signal is transmitted through the wall 320 towards the person 340 positioned behind the wall 320. This portion of the transmitted signal is reflected off of the person's body (e.g., thorax), as the person is breathing, back towards the Doppler radar module 120. This reflected signal 334 is detected and received by the Doppler radar module 120. The power received from the wall 320 by the Doppler radar module 120 is amplified and converted to a voltage that is sampled by the computer control system 150 at typically 512 discrete positions of the rotating mirror 112 as it scans 180 degrees across the target area and 180 degrees along the back of the radar antenna scanner assembly that is lined with radar absorbing material (RAM).

Figure 4:
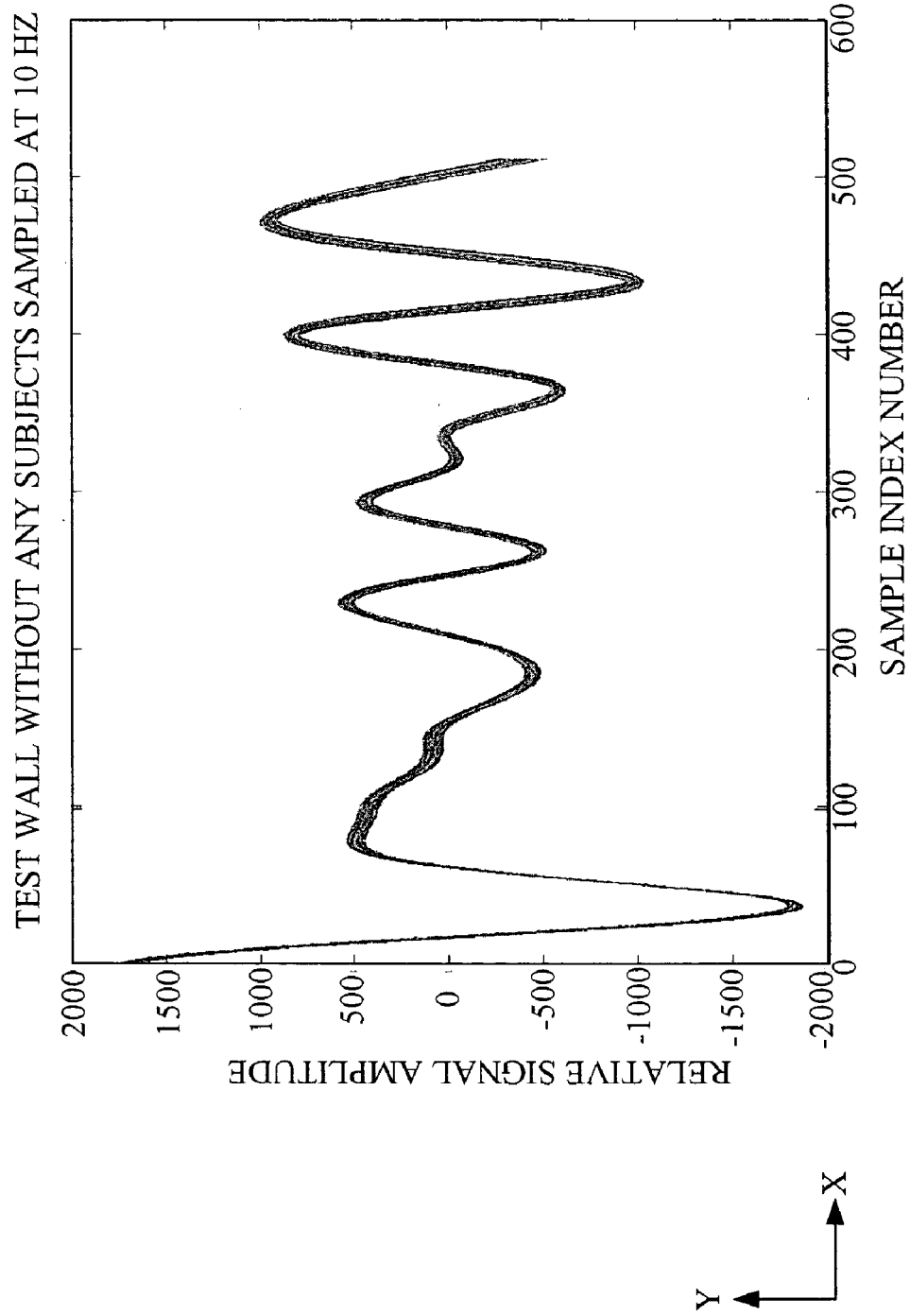
FIG. 4 is a graphical plot of the signals produced by the radar detection device 100 of FIG. 1 when there is no subject in a target area.

FIG. 4 is a plot of antenna position versus signal amplitude when there is no person 340 positioned behind the wall 320. Further, radar detection device 100 is mounted on a tripod in a stationary position. Here, the scanner 110 rotates the antenna beam, via the 45-degree mirror 112, from the left to the right across the test wall 320 with the tangential point of the scan being the center of the wooden door in the middle of the wall (a beam position at approximate data point 295 in FIG. 4). The 'Y' ordinate of FIG. 4 represents the relative voltage of the signal that is produced by the scanning operation after approximately 50 dB of amplification and some high and low pass filtering. There is variation in the received signal amplitude from scan to scan, as evidenced by the broadening of the plotted amplitude when 976 of the 512-point scans are overlaid on top of each other, as shown in FIG. 4. Note, this plot line broadening is insignificant compared to total signal amplitude.

The assembly of the scanner is covered across the rear around 180 degrees of rotation by the RAM. Accordingly, the antenna scans the RAM from data point 25 to approximate data point 180, as measured along the X-axis of FIG. 4. From data sample point 180 to approximate sample point 512 of FIG. 4, the antenna beam is radiated toward the wall—being first swept across the leftmost test wall made of wood siding on the outside and wall board on the inside surface, then across the solid wooden door, located in the center of the test wall, and finally across the rightmost brick wall with 2 by 4 headers and wall board backing—before the beam encounters the RAM again. The amplitude variation in the sinusoidal shaped trace shown in FIG. 4 is called antenna scan modulation. Antenna scan modulation is produced by a change in antenna path length as the scan moves from the left of the wall to the right of the wall while encountering smooth wall surface and recessed and extended trim on the wall surface. The center of the wall scan position represents the shortest length path to the wall. This change in path length causes a proportional change in the electrical phase of the transmitted and received signal, which is detected by the radar. The amplitude of the scan modulation is determined by wall or target radar reflectivity at the antenna position.

Figure 5:
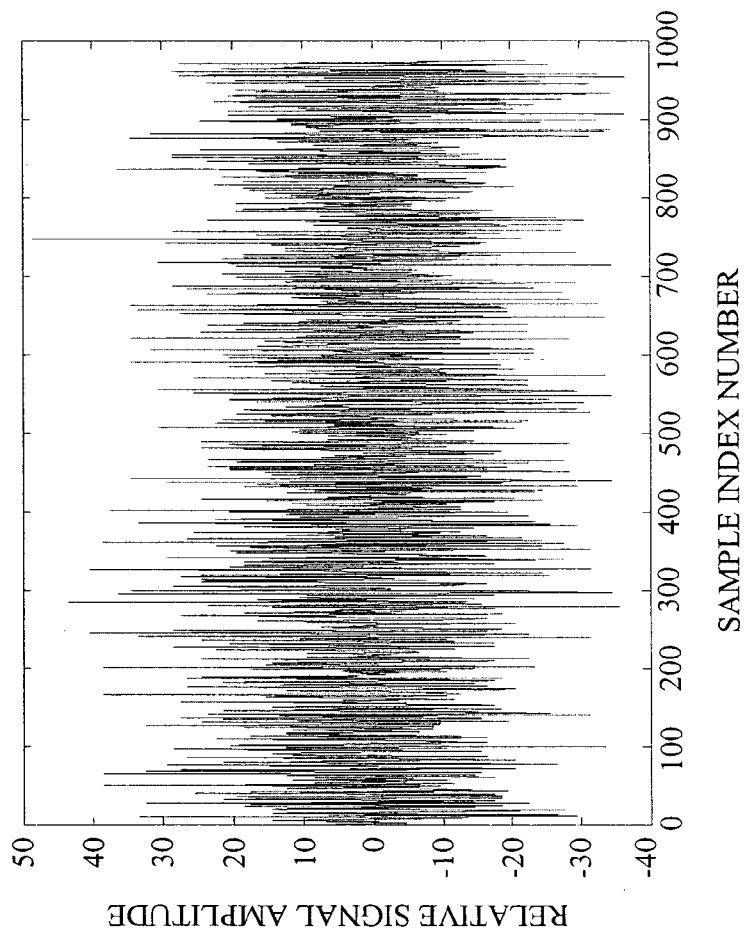
FIG. 5 is graphical plot of the amplitude of the signal produced in FIG. 4 for one discrete position along a horizontal scanning axis without a subject behind the wall.

FIG. 5 is a plot of 976 data points (from single sample index number position 195 shown in FIG. 4.) that were taken each time the scanner rotated through 360 degrees and reached sample point 195. Note, time increases in FIG. 5 from left to right. Data point 195 corresponds to the location of the scanning mirror 112 when the antenna beam is pointed at the wood siding wall to the left of the door in the center of the wall 320. Here, there is no person 340 behind the wall 320. Referring to FIG. 5, the maximum peak voltage value at data point 195 is no greater than plus or minus 40 voltage units over the entire 976 scans. This is a small variation compared to the variations observed when a profile is produced of a subject standing behind the wall and breathing, as will be shown. Some of the randomness of the plot shown in FIG. 5 is presumed to be system noise and vibration effects from the scanner motor used in this particular test.

Figure 6:
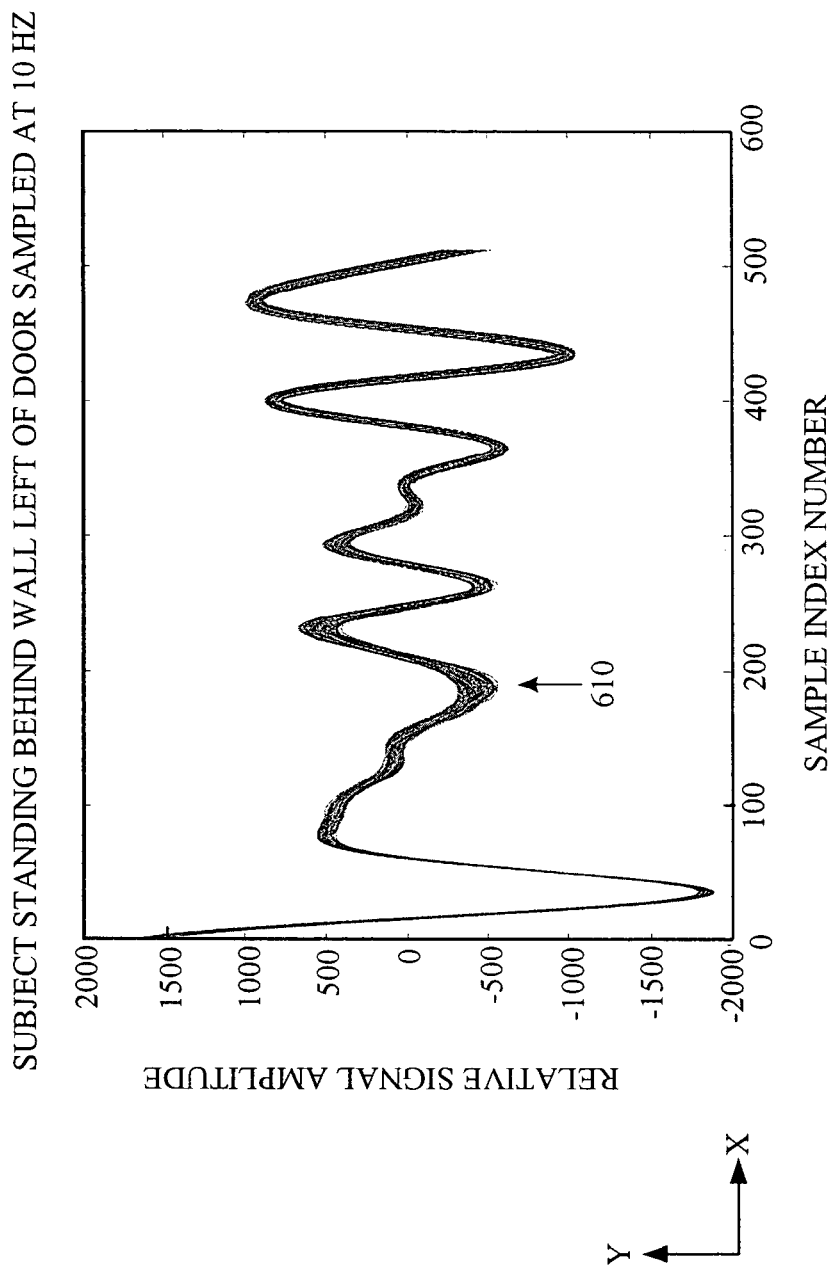
FIG. 6 is a graphical plot of the signals produced by the radar detection device of FIG. 1 when there is a subject present in a target area, and the subject is positioned behind a wooden construction wall.

FIG. 6 shows a plot of 976 antenna scans, each containing 512 points of data taken over 360 degrees of antenna rotation with a human subject standing rigid behind the wood siding test wall to the left of the door (at sample point 195). The subject was requested to breathe every five seconds. Referring to FIG. 6, a broadening in the line width can be observed around data point 195, as indicated by pointer 610, representing the azimuth where the subject was located. The amplitude broadening around peak 195 is the result of movement of the test subject's thorax area when breathing. Sample point 195 is the center of the subject's location along the X-axis. Since the antenna pattern is approximately 16 degrees to the half power points, there is a spread around the center at sample point 195. As previously stated, the amplitude of the "wall reflection" is very large, and the amplitude of the reflection from the target individual 340 behind the wall 320 is very small. Yet, the respiration signature at pointer 610 is recognizable as a broadened area along the plot generated by the radar detection device 100 employing the radar scanner 110.

Figure 7:
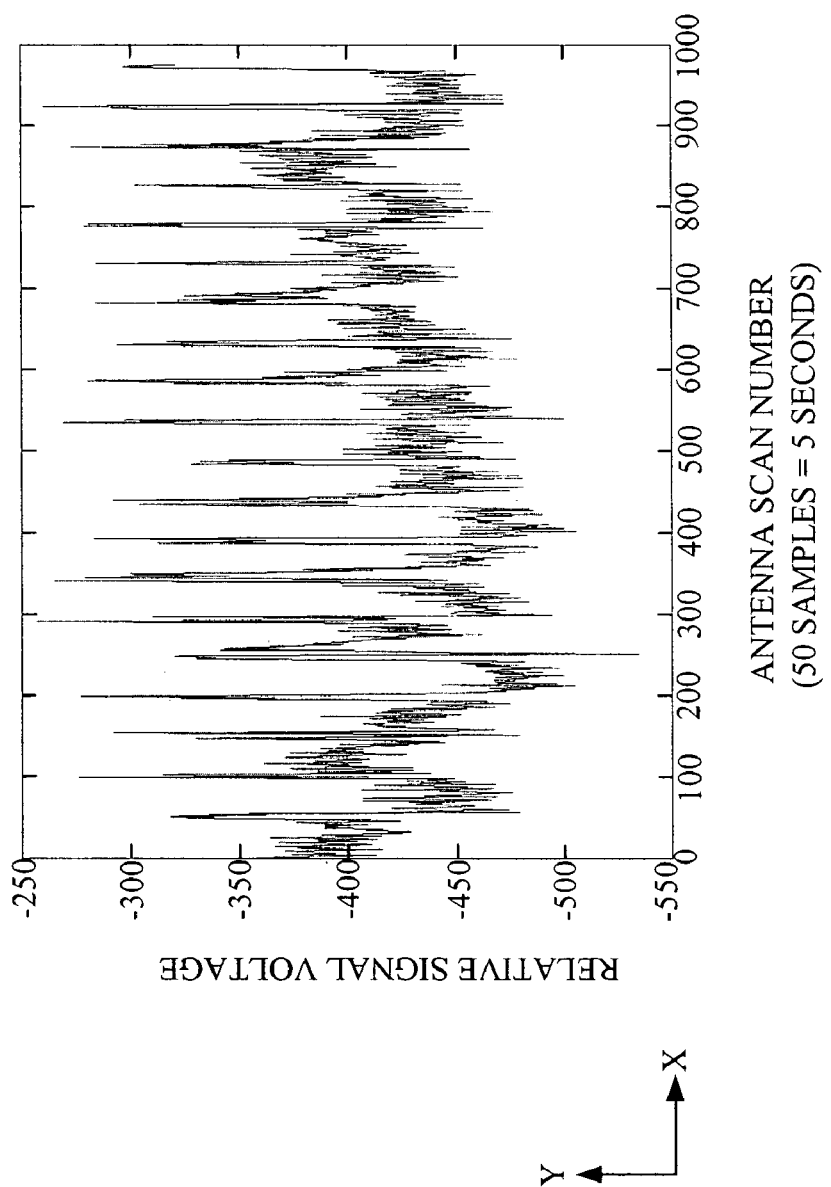
FIG. 7 is a graphical plot of the signals produced in FIG. 6 for one discrete position along a horizontal scanning axis, with over 900 scans, showing the respiration signature of the subject behind a wooden wall as a function of time.

FIG. 7 is a plot of the amplitude of 976 data points, each taken from sample point position 195, as shown in FIG. 6. The data is taken from sample point 195 from each successive array stored in the signal processor 140. Note, time increases in FIG. 7 from left to right. In FIG. 7, data point 195 corresponds to the location of the scanning antenna when the antenna beam is pointed to the left at the wood siding wall behind which the human subject or target 340 is standing. Note, the target subject 340 was requested to breathe once every five seconds. Further note that the sample was taken at point 195 ten times each second. Thus, every 50 sample points shown in FIG. 7 represents five seconds of elapsed time. The plot of FIG. 7 shows a spike every 50 points demonstrating that there is a respiration event detected every five seconds. Accordingly, the spikes in signal level are an indicator that there is a breathing person 340 behind the wall 320. The frequency of occurrence of the respiration spike events confirms that a periodic event is being observed.

The peak to peak amplitude of the signal of the trial with the person 340 behind the wall is 250 voltage units compared to the peak to peak level of 80 voltage units shown in FIG. 4 when there is no person 340 behind the same wall. Therefore, the data in FIG. 7 shows that the radar detection device 100 has detected the respiration signature of a subject standing behind the wall to the left of the door. This data also shows that even with the radar scanner 110 located approximately three feet from the door, the peak to peak amplitude of the respiration signal is strong compared to the case where there is no subject behind the wall.

Figure 8:
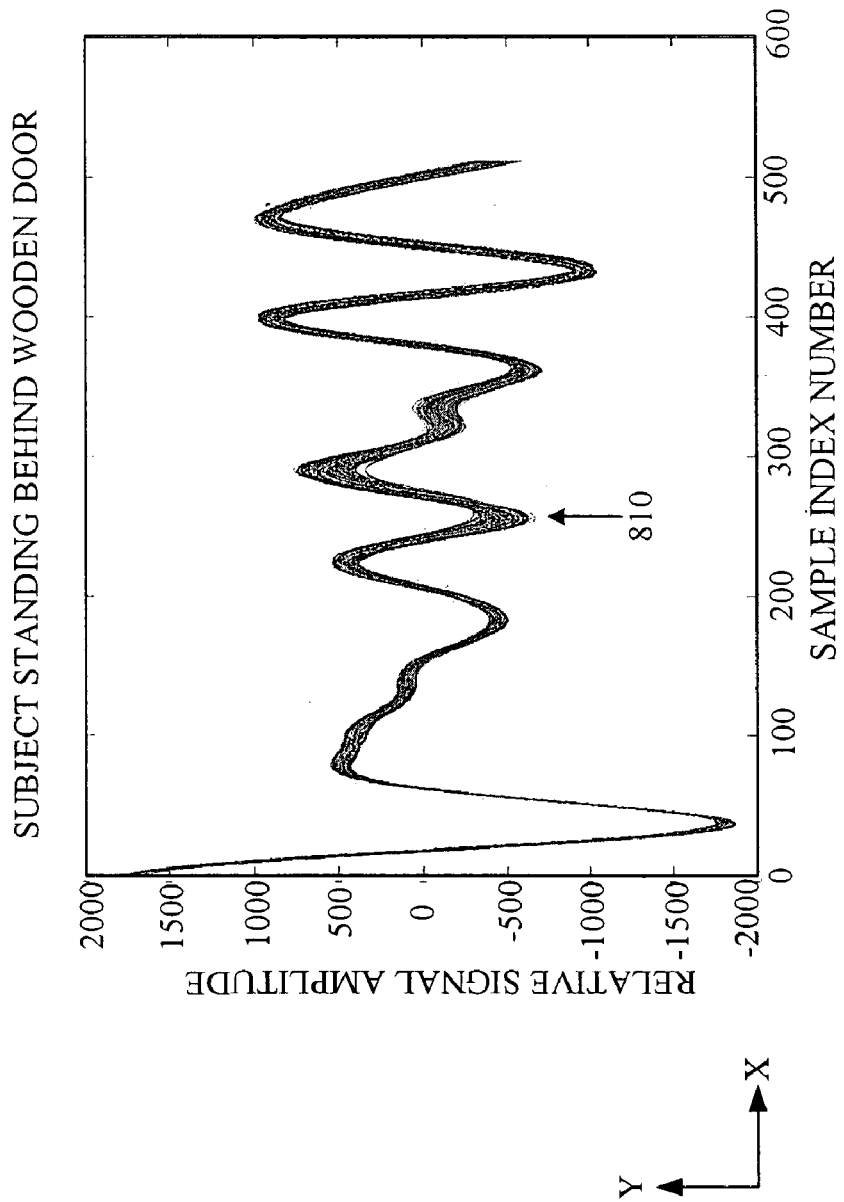
FIG. 8 is a graphical plot of the signals produced by the radar detection device of FIG. 1 for one discrete position along a horizontal scanning axis when the subject is positioned behind a wooden door.
Figure 9:
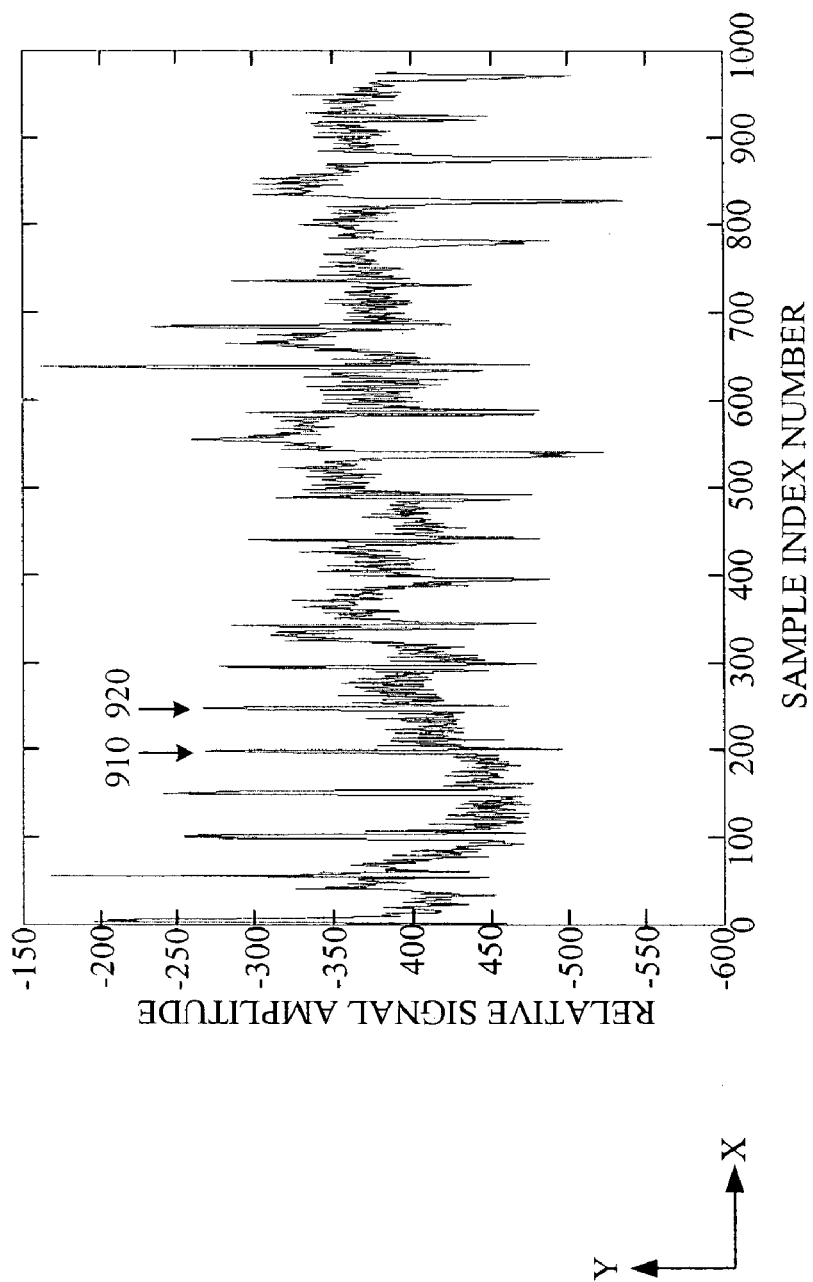
FIG. 9 is a graphical plot of the signals produced in FIG. 8 for one discrete position along a horizontal scanning axis, with over 900 scans, showing the respiration signature of the subject behind a wooden door as a function of time.

Next, FIG. 8 shows 976 antenna scans overlaid on each other, each comprised of 512 sample points on a single plot when the subject is located behind the wooden door in the center of the wall. Note, the broadening in the plotted line of the X-axis now occurs at sample point 250 (the position of pointer 810) because the subject has moved down the wall, from a point to the left of the door to a position behind the door. Accordingly, FIG. 9 is a plot of 976 successive data points taken from sample point position 250 in FIG. 8 (at pointer 810). Note, respiration events at pointers 910 and 920 occur every five seconds and repeats every 50 samples which indicates that a living subject 340 is behind the wall at the azimuth that corresponds to sample point 250 in FIG. 8. Once more, the maximum peak to peak amplitude shown in FIG. 9 is much greater than shown in FIG. 4, providing a secondary indication of a subject's presence.

Figure 10:
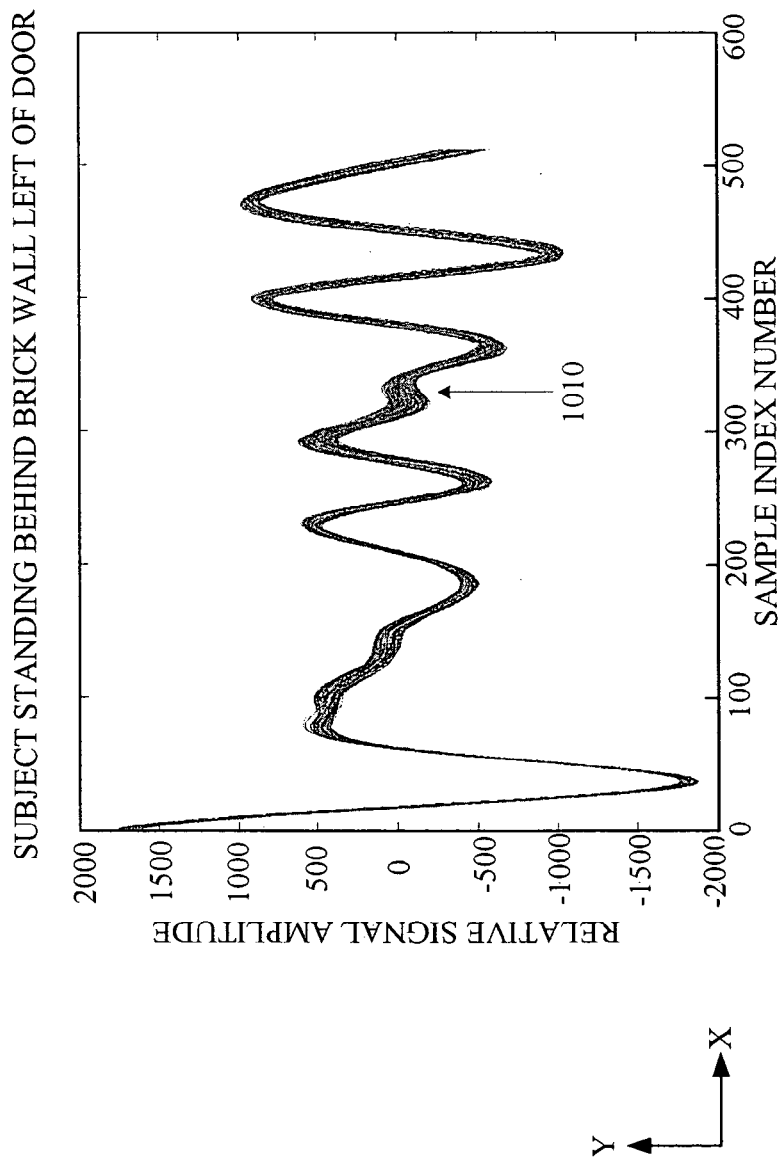
FIG. 10 is a graphical plot of the signals produced by the radar detection device of FIG. 1 when there is a subject present in the fringe of the target area with the subject positioned behind a brick wall.
Figure 11:
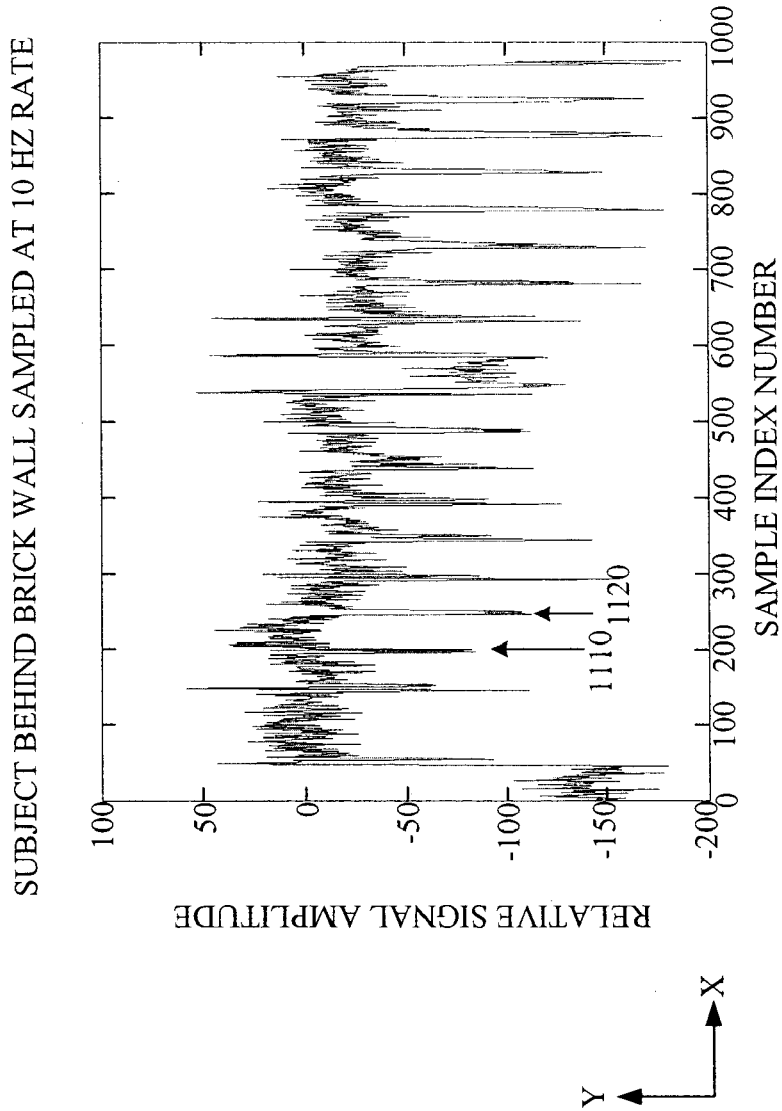
FIG. 11 is a graphical plot of the signals produced in FIG. 10 for one discrete position along a horizontal scanning axis, with over 900 scans, showing the respiration signature of the subject behind a brick wall, as a function of time.

Diversely, FIG. 10 shows all 976 antenna scans on a single plot when the subject is located behind the brick wall on the far right of the wall 320. The broadening along the X-axis now occurs at sample point 325 (as indicated by pointer 1010) because the subject has moved down the wall from the door toward the right to a position behind the brick wall. Correspondingly, FIG. 11 shows the respiration signature of the subject behind the brick wall when one data point from each of the 976 scans taken at sample point 325 is plotted in time. Note, the respiration signature of one cycle every five seconds (as noted by the timing highlighted by pointers 1110 & 1120) has a high signal to noise ratio, even though the subject is standing behind an absorptive brick wall with the scanner 110 set back three feet from the door and the living subject 340 at an off angle from the scanner.

Figure 12:
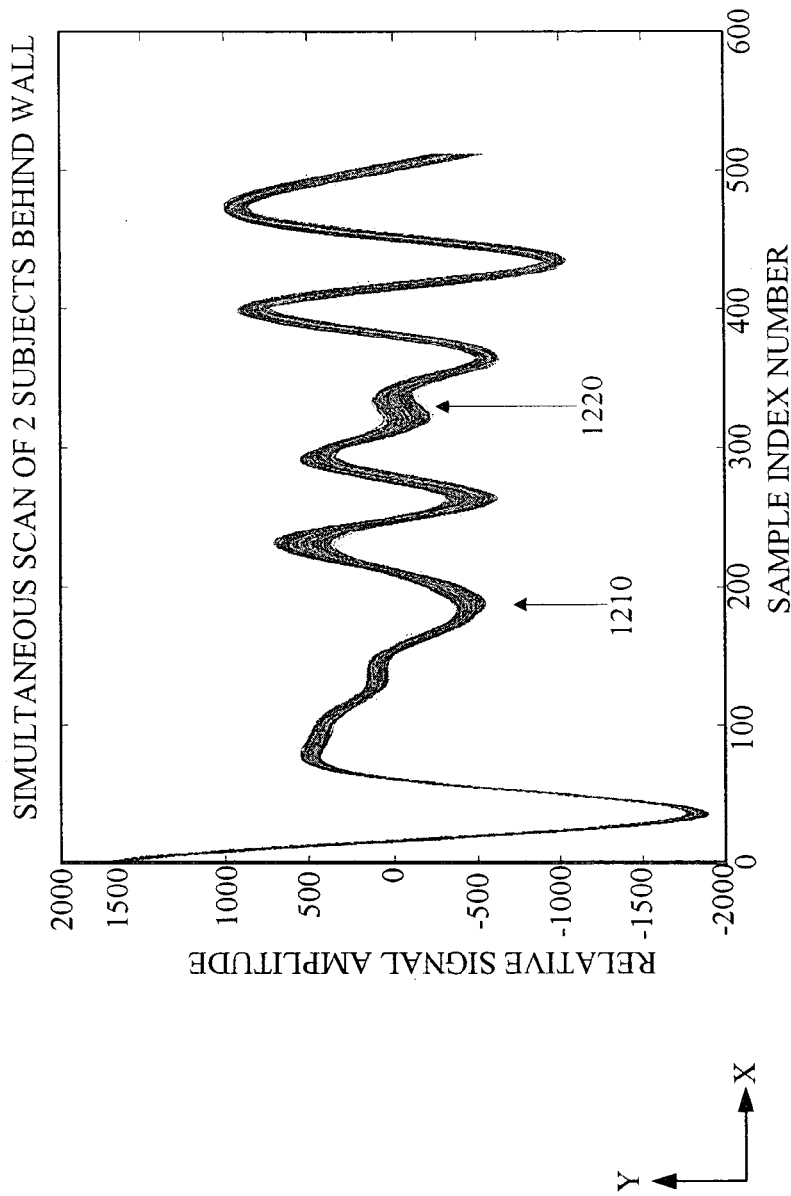
FIG. 12 is a graphical plot of the signals produced by the radar detection device of FIG. 1 when there are two subjects present in the target area (one subject is positioned behind a wooden wall and another subject is positioned behind a brick wall).

In addition, the radar detection device 100 also has the ability to detect and resolve two subjects simultaneously behind the wall 320, standing five feet apart. In this example, a first test subject was requested to stand behind the wall at the left of the door and a second subject was requested to stand to the right of the door behind the brick wall. FIG. 12 shows the results when 976 scans of the brick wall are laid on top of each other. The center of broadening along the X-axis appears at sample point 195 and 325, as indicated by pointers 1210 & 1220. Given the 16-degree antenna 3 dB beamwidth, the broad response pattern around these center points is expected, especially in the area between sample points 195 and 325 where there may be energy from the respiration signature from both subjects.

Figure 13:
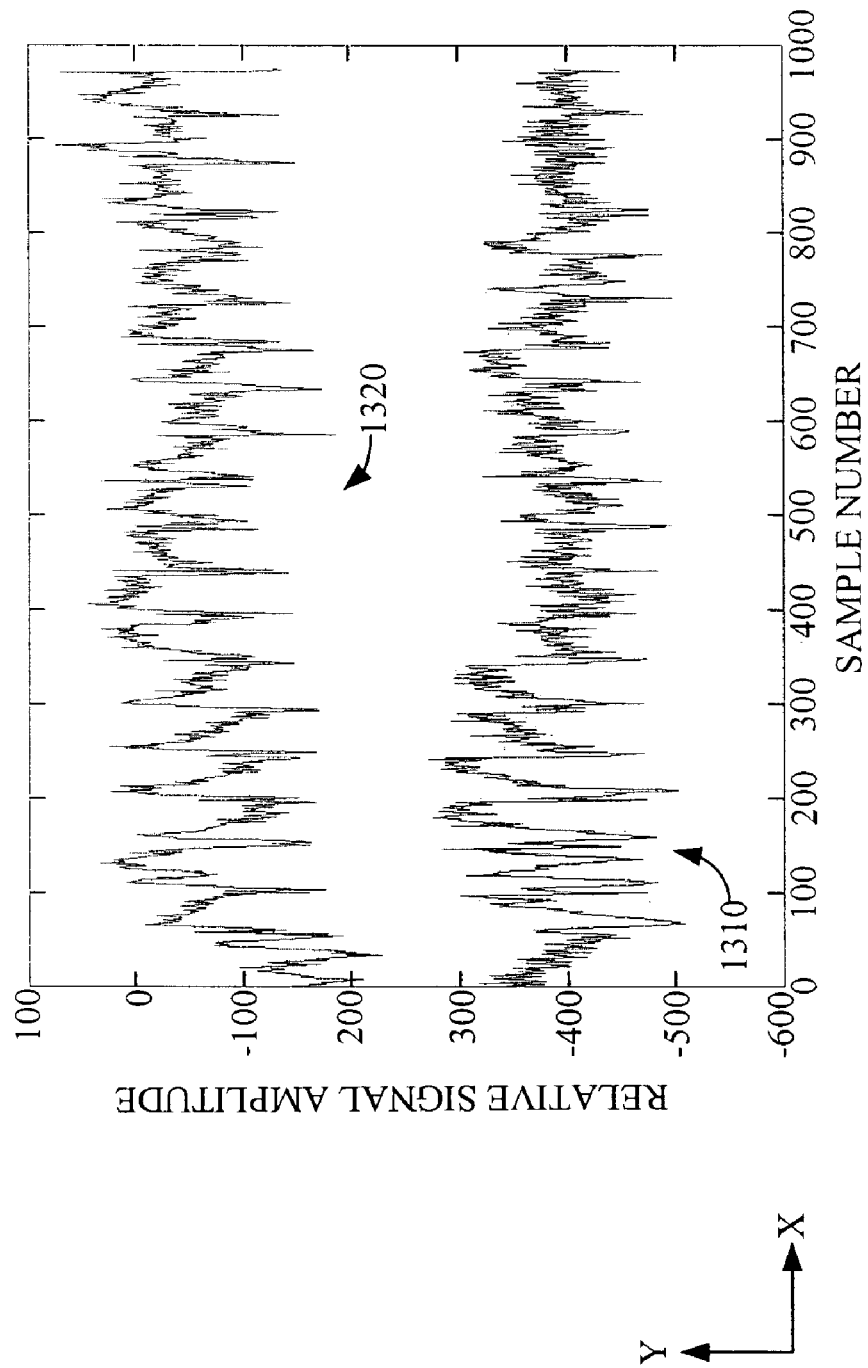
FIG. 13 is a graphical plot of the signals produced in FIG. 12 for one discrete position along a horizontal scanning axis, with over 900 scans, showing the respiration signature of one subject behind the wooden wall and one subject behind a wooden door, as a function of time.

Next, FIG. 13 shows the time profile when one data point was sampled for each of the 976 scans at sample points 195 and 325 (also marked by pointers 1210 and 1220 in previous diagram FIG. 12) that corresponds to the location of each subject. The lower plot 1310 is from the subject standing behind the wall section that is to the left of the door sampled along data point 195 in FIG. 12. The upper plot 1320 shows the simultaneous time profile of the subject standing behind the brick wall that is to the right of the door sampled in time along data point 325.

Referring to FIG. 13, energy from the first subject does not appear to mix with the energy from the second subject, although the antenna features a broad 16-degree 3 dB beamwidth, and the subjects are spaced within five feet of each other. Note, the subject behind the brick wall began breathing every five seconds before the subject behind the wall (bottom) began breathing every five seconds. As a result, the peak in, the respiration signature from the first subject shown in 1320 does not occur at the same time as the respiration signature from the second subject 1320. Thus, the fact that the radar detection device 100 can separate the respiration signature of relatively closely spaced subjects has been demonstrated. Further, FIG. 13 also shows that the subject behind the wall section (bottom plot 1310) stopped breathing at the request of the radar operator between scan (sample points) 775 through 976 of the test while the subject behind the brick wall (top plot 1320) continued to breath once every five seconds during this interval.

As shown, the stationary tripod mounted radar detection device 100 employing the radar scanner 110 has the capability to locate multiple subjects behind a wall or other opaque reflective surface and to provide a good indication of their location in relation to antenna reflector or mirror 112 position when the sample number is converted to azimuth. Further, multiple breathing subjects may also be detected simultaneously, and each may be located in azimuth. In addition, the radar detection device 100 employing the scanner 110 may be located at a substantial distance (e.g., three or more feet) from the wall being scanned. As discussed below, the radar detection device 100 may also operate in a hand held mode. So, in FIG. 14, data was recorded when the test subject was standing behind the door and the radar detection device 100 was hand held three feet from the door in order to evaluate the magnitude of the artifacts that the hand held radar detection device 100 produced along with the amplitude of the respiration signals produced.

Figure 14:
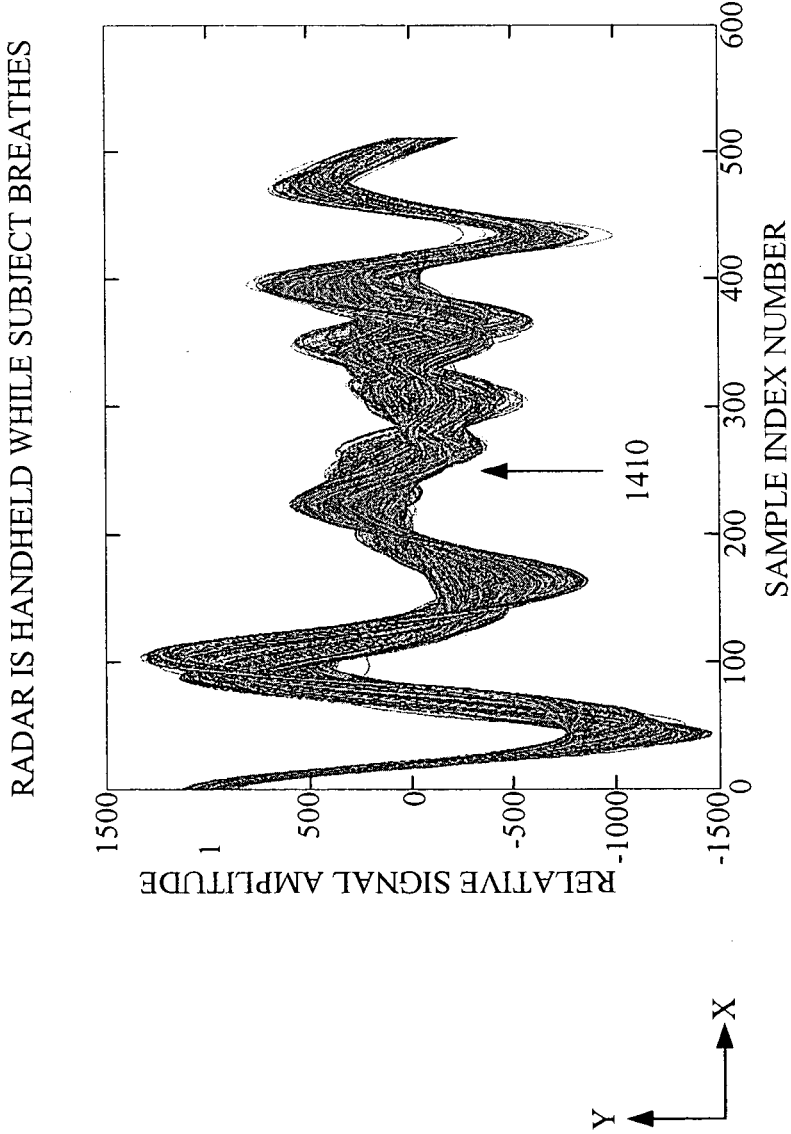
FIG. 14 is a graphical plot of signals produced by the radar detection device of FIG. 1 when there is one subject behind a door and the radar detection device is being hand held demonstrating how the motion associated with hand holding the radar can mask the slight motion of the subject.

In particular, FIG. 14 shows 976 antenna scans overlaid on a single plot while the radar detection device 100 is hand held. Referring to FIG. 14, the baseline of the plot is very broad along the Y-axis, indicating that hand motion introduced random radar signals (clutter) that also extended across the entire plot along the X-axis. Normally, the Doppler radar nodule 120 does not produce an output unless there is motion of one of the following elements: (1) the Doppler radar module itself, (2) an intervening surface (wall or door), or (3) a moving human target behind the intervening surface. The scanning antenna assembly (e.g., scanner 110 and vertical antenna 125) introduces motion due to an effect called antenna scan modulation. For example, assume that the radar detection device 100 with the rotating mirror 112 is set up three feet from an absolutely flat wall. As the mirror scans from left to right, the 16-degree beam paints an approximate one foot radiation pattern in the shape of ellipse on the wall, except when the beam is exactly tangential to the wall. At the tangential point, the beam is described as a circle. When the beam is at the left or right far end of the wall, the path between the radar detection device 100 and the end of the wall is longer than when the beam is directed at the tangential point on the wall directly in front of the radar detection device 100. This collapse of the path length as the beam scans the wall introduces the synthetic motion called antenna scan modulation. The amplitude of the scan modulation is dependent on the radar reflectivity of the object being scanned.

Figure 15:
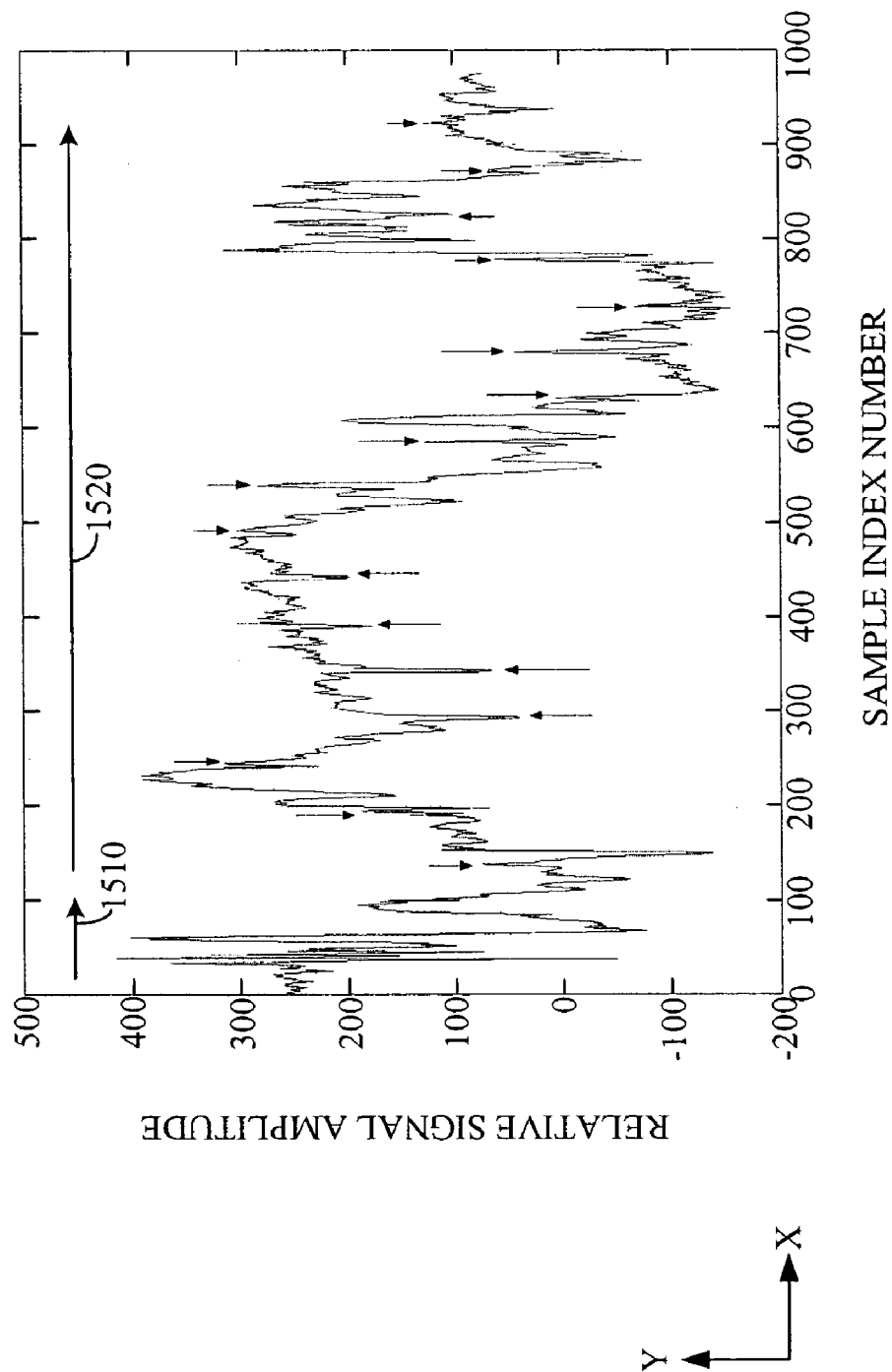
FIG. 15 is a graphical plot of the signals produced in FIG. 13 for one discrete position along a horizontal scanning axis, with over 900 scans, showing the masking of hand motion when the radar detection device is being moved by hand, and also when the user is attempting to limit hand motion to a minimum amount.

Note, in the example demonstrated by FIG. 14, (although it is hard to detect given the intense hand motion induced clutter), the subject stood behind the door at approximate scan position 250, as indicated by pointer 1410. As shown in FIG. 14, hand movement generates strong reflections from the wall and covers evidence of the subject's presence. Next, in FIG. 15, a plot of each of the successive data points collected at sample point 250 (pointer 1410) for 976 rotations of the antenna is shown. Here, the test subject was instructed to breathe once every five seconds. Accordingly, the first 100 samples experience heavy clutter effects while the radar was being picked up and positioned by hand, as indicated by pointer 1510. Then, the radar was held as stable as possible during the remaining time shown, as indicated by pointer 1520. The final increment starting at sample point 101 and ending at sample point 976 in the plot shows both the respiration signals, marked by a vertical arrows, and the radar clutter that was produced by the hand motion. As shown, the respiration events that occur every five seconds are recognizable, and each are marked by a vertical arrow. Thus, a respiration signature is observable when the radar detection device 100 are operated in a hand held mode, although the observed respiration events are small compared to the motion clutter signal generated by the reflections of the radar signal off of the intervening wall when the operator's hand is moving the radar detection device 100 in an exaggerated manner.

Figure 16:
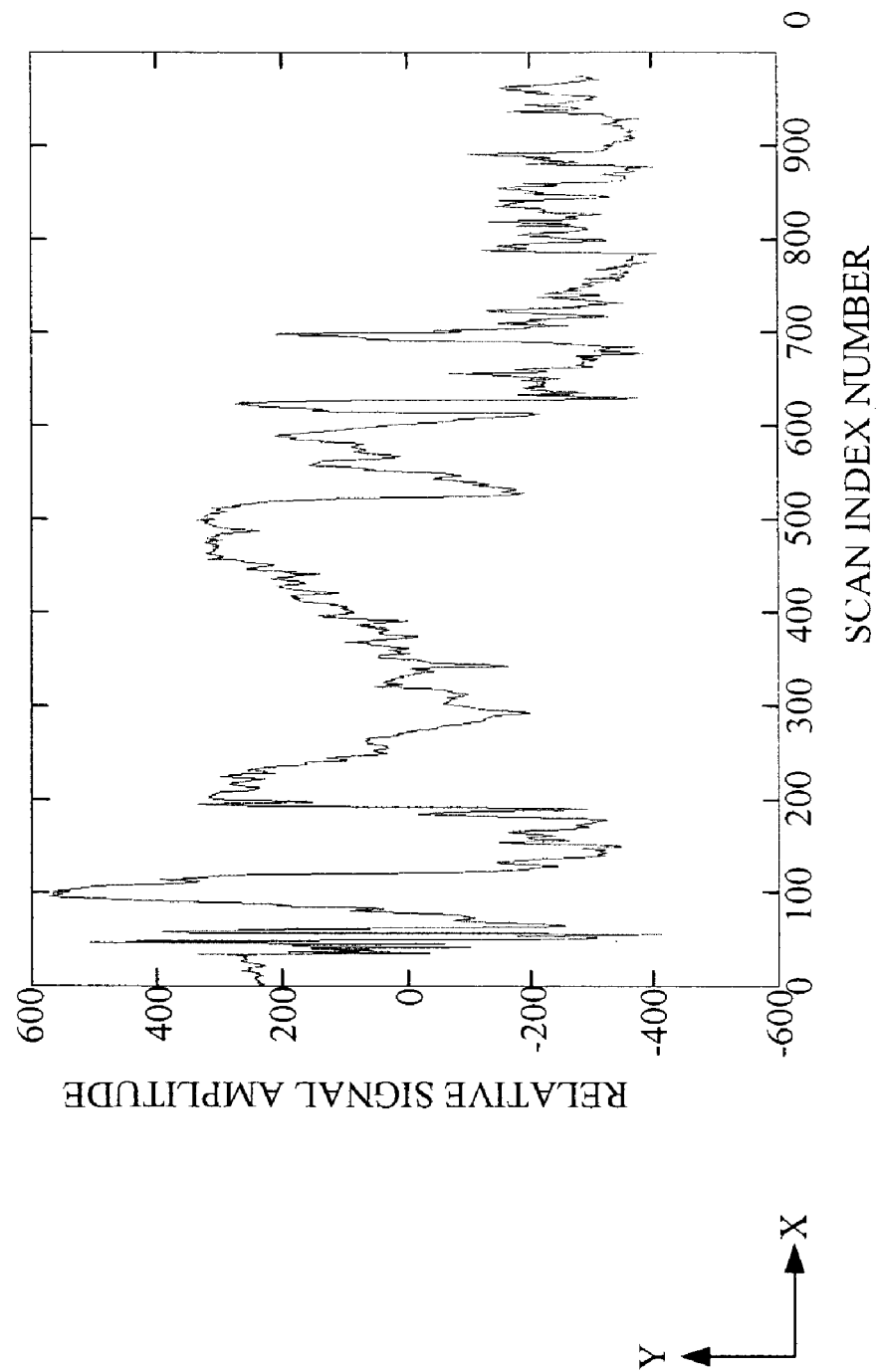
FIG. 16 is a graphical plot of data that was collected at sample index number 350 of FIG. 14 in over 900 scans of the radar detection device of FIG. 1.

Next, FIG. 16 shows a plot of the data that was collected at sample index number 350 (from FIG. 14) over 976 scans of the radar detection device 100. This plot represents data collected when the antenna beam is illuminating the brick wall while the subject was located six feet to the left behind the wood wall. There is little or no respiration information seen in this plot. FIG. 16 demonstrates that both the data in FIG. 15 and FIG. 16 contain the hand motion signal but only FIG. 15 contains recognizable amounts of both the hand motion and the respiration signature of the human subject. Using data from FIG. 16 the signal processor 140 may perform the mathematical equivalent of subtraction to remove the hand motion in FIG. 15, leaving a more clutter free record of respiration in FIG. 16.

The signal processor 140 and control system 150 components and modules of embodiments of the present invention can be implemented in hardware, software, firmware, or a combination thereof. If implemented in hardware, as in preferred embodiment(s), the signal processing components can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc. In alternative embodiment(s), the signal processor 140 and control system 150 components are implemented in software or firmware that is stored in a memory and that is executed by a suitable instruction execution system.

Any process descriptions or blocks in flow charts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A system for detecting a respiration signal of at least one subject in a target area, comprising:
    a scanning antenna to transmit a microwave signal across the target area, wherein the scanning antenna receives a reflected microwave signal from the at least one subject;
    a control system to track the position of the scanning antenna as the scanning antenna transmits the microwave signal while the position of the scanning antenna mechanically and continuously rotates;

a signal processing system to detect the respiration signal of the at least one subject from the reflected microwave signal that is received by the scanning antenna.

2. The system of claim 1, further comprising: a Doppler radar module
to generate the microwave signal.

3. The system of claim 2, wherein the Doppler radar module operates at 10.525 GHz.

4. The system of claim 1, further comprising: radar absorbing material to restrict the area that the scanning antenna transmits.

5. The system of claim 4, the control system further comprising: a digital shaft encoder to provide positional information of the scanning antenna.

6. The system of claim 1, further comprising: a display device to display a graphical plot of the reflected microwave signal.

7. The system of claim 6, wherein the control system samples the reflected signal at discrete positions of the scanning antenna and compiles the sampled data to produce the graphical plot.

8. The system of claim 6, wherein the control system samples the reflected signal at one discrete position of the scanning antenna and compiles the sampled data to produce the graphical plot.

9. The system of claim 6, wherein the position along the horizontal scanning axis of the at least one subject is ascertained from the graphical plot.

10. The system of claim 1, wherein one subject is positioned behind a reflective surface in the target area.

11. The system of claim 1, wherein two subjects are positioned behind a reflective surface in the target area and the respiration signature of each subject is detected.

12. The system of claim 1, wherein the scanning antenna is being operated in a hand held mode.

13. A system for detecting a respiration signal of at least one subject in a target area, comprising:
means for transmitting a microwave signal across the target area in a horizontal scanning motion;
means for receiving a reflected microwave signal from the target area;
means for tracking the position of the means for transmitting as the means for transmitting transmits the microwave signal while the means for transmitting mechanically and continuously rotates;
means for detecting the respiration signal of the at least one subject, wherein the reflected microwave signal was from the at least one subject.

14. The system of claim 13, wherein the means for transmitting operates at 10.525 GHz.

15. The system of claim 13, further comprising: means for displaying a
graphical plot of the reflected microwave signal.

16. The system of claim 15, further comprising:
means for sampling the received reflected microwave signal at at least one discrete position of the means for transmitting;
and means for compiling sampled data to produce the graphical plot.

17. The system of claim 16, wherein the means for detecting processes sampled data from the received reflected microwave signal to remove an undesired signal caused by self-induced motion of the system.

18. The system of claim 17, wherein the means for detecting processes the sampled data by subtracting data having the undesired signal from data having the undesired signal and the respiration signal.

19. The system of claim 16, wherein the means for tracking samples the reflected signal at only one discrete position.

20. The system of claim 15, wherein the position along the horizontal scanning axis of the at least one subject is ascertained from the graphical plot.

21. The system of claim 13, wherein one subject is positioned behind a reflective surface in the target area.

22. The system of claim 13, wherein two subjects are positioned behind a reflective surface in the target area and the respiration signature of each subject is detected.

23. The system of claim 13, wherein the means for transmitting is being operated in a hand held mode.

24. A method for detecting a respiration signal of at least one subject in a target area, comprising the steps of:
continuously and mechanically rotating a scanning antenna that is transmitting a microwave signal across the target area along a horizontal scanning axis;
receiving a phase modulated reflected microwave signal from the target area;
tracking the position at which the microwave signal is transmitted along the horizontal scanning axis;
detecting the phase shifted respiration signal of the at least one subject, wherein the reflected microwave signal was from the at least one subject.

25. The method of claim 24, wherein the frequency of the microwave signal is 10.525 GHz.

26. The method of claim 24, further comprising the step of: displaying a graphical plot of the reflected microwave signal.

27. The method of claim 26, further comprising the steps of:
sampling the received reflected signal at at least one discrete position along the horizontal scanning axis;
and compiling processed sampled data to produce the graphical plot.

28. The method of claim 27, further comprising the step of: processing the sampled data by performing the mathematical equivalent of subtraction of scanner positions containing only hand motion induced clutter data from scanner positions containing both the hand motion and the respiration signal.

29. The method of claim 26, wherein the received reflected signal is sampled at only one discrete position.

30. The method of claim 26, further comprising the step of:
ascertaining the position along the horizontal scanning axis of at least one subject from the graphical plot.

31. The method of claim 24, wherein one subject is positioned behind a reflective surface in the target area.

32. The method of claim 24, wherein two subjects are positioned behind a reflective surface in the target area and the respiration signature of each subject is detected.

33. The method of claim 24, wherein the transmitting step is being performed in a hand held mode.

* * * * *